US008715221B2

(12) United States Patent
Curtin et al.

(10) Patent No.: US 8,715,221 B2
(45) Date of Patent: May 6, 2014

(54) WEARABLE KIDNEY

(75) Inventors: Conor Curtin, Westford, MA (US);
Benjamin J. Lipps, Boston, MA (US);
Norma J. Ofsthun, Lexington, MA
(US); Harold F. Sandford, Groton, MA
(US)

(73) Assignee: Fresenius Medical Care Holdings, Inc.,
Lexington, MA (US)

( * ) Notice: Subject to any disclaimer, the term of this patent is extended or adjusted under 35 U.S.C. 154(b) by 829 days.

(21) Appl. No.: 11/371,216

(22) Filed: Mar. 8, 2006

(65) Prior Publication Data
US 2007/0213665 A1   Sep. 13, 2007

(51) Int. Cl.
*A61M 1/00* (2006.01)
(52) U.S. Cl.
USPC ............................................. 604/29; 604/5.01
(58) Field of Classification Search
USPC ..................... 604/29, 5.01; 424/44
See application file for complete search history.

(56) References Cited

U.S. PATENT DOCUMENTS

| | | |
|---|---|---|
| 3,579,441 A | 5/1971 | Brown |
| 3,707,967 A | 1/1973 | Kitrilakis et al. |
| 3,825,493 A | 7/1974 | Brown et al. |
| 4,094,775 A | 6/1978 | Mueller |
| 4,256,102 A | 3/1981 | Monaco |
| 5,026,365 A | 6/1991 | Rossini et al. |
| 5,284,470 A | 2/1994 | Beltz |
| 5,350,357 A | 9/1994 | Kamen et al. |
| 5,409,903 A | 4/1995 | Polak et al. |
| 5,549,674 A | 8/1996 | Humes et al. |
| 5,902,336 A | 5/1999 | Mishkin |
| 5,944,684 A * | 8/1999 | Roberts et al. ............ 604/5.04 |
| 6,217,859 B1 | 4/2001 | Chang et al. |
| 6,234,991 B1 | 5/2001 | Gorsuch |
| 6,254,567 B1 | 7/2001 | Treu et al. |

(Continued)

FOREIGN PATENT DOCUMENTS

| | | |
|---|---|---|
| DE | 25 58 363 | 7/1977 |
| DE | 31 10 128 A1 | 9/1982 |

(Continued)

OTHER PUBLICATIONS

O'Loughlin, J.A. et al., "In Vivo and in Vitro Degradation of Urea and Uric Acid by Encapsulated Genetically Modified Microorganisms," Tissue Engineering, 10(9/10): 1446-1455 (2004).*

(Continued)

*Primary Examiner* — Theodore Stigell
*Assistant Examiner* — Deanna K Hall
(74) *Attorney, Agent, or Firm* — Hamilton, Brook, Smith & Reynolds, P.C.

(57) ABSTRACT

The present invention relates to a wearable peritoneal dialysis system and a replaceable cartridge in the wearable peritoneal dialysis system that regenerates the peritoneal dialysis solution without removing essential ions from the solution and, consequently, the patient. The invention also relates to methods of removing uremic waste metabolites from a patient using the wearable peritoneal dialysis system. A source of one or more enzymes that degrades uremic waste metabolites can be administered orally in conjunction with use of the wearable peritoneal dialysis system such that the load of toxins needing to be eliminated by the wearable peritoneal dialysis system is reduced. The wearable peritoneal dialysis system is meant to operate continuously or semi-continuously, its components small and light enough that it can be comfortably worn by a patient constantly, without burden.

38 Claims, 7 Drawing Sheets

Hollow Fiber Cartridge: Ion Rejecting Skin

(56) References Cited

U.S. PATENT DOCUMENTS

| | | | |
|---|---|---|---|
| 6,579,460 | B1 | 6/2003 | Willis et al. |
| 6,706,287 | B2 | 3/2004 | Ranganathan et al. |
| 6,719,907 | B2 | 4/2004 | Collins et al. |
| 6,960,179 | B2 | 11/2005 | Gura |
| 7,033,498 | B2 | 4/2006 | Wong |
| 7,208,092 | B2 | 4/2007 | Micheli |
| 7,276,042 | B2 | 10/2007 | Polaschegg et al. |
| 7,309,323 | B2 | 12/2007 | Gura et al. |
| 7,597,677 | B2 | 10/2009 | Gura et al. |
| 7,867,214 | B2 * | 1/2011 | Childers et al. ............... 604/411 |
| 8,012,118 | B2 | 9/2011 | Curtin et al. |
| 2002/0052571 | A1 | 5/2002 | Fazio |
| 2002/0112609 | A1 * | 8/2002 | Wong .............................. 96/131 |
| 2002/0123715 | A1 | 9/2002 | Sorenson et al. |
| 2003/0050622 | A1 | 3/2003 | Humes et al. |
| 2003/0105424 | A1 | 6/2003 | Karoor et al. |
| 2003/0114787 | A1 | 6/2003 | Gura |
| 2004/0019312 | A1 | 1/2004 | Childers et al. |
| 2004/0082903 | A1 | 4/2004 | Micheli |
| 2004/0254514 | A1 | 12/2004 | Gura |
| 2005/0123529 | A1 | 6/2005 | O'Loughlin et al. |
| 2005/0131332 | A1 | 6/2005 | Kelly et al. |
| 2006/0058731 | A1 | 3/2006 | Burnett et al. |
| 2007/0060786 | A1 | 3/2007 | Gura et al. |
| 2007/0161113 | A1 | 7/2007 | Ash |
| 2007/0179431 | A1 | 8/2007 | Roberts et al. |
| 2007/0199898 | A1 | 8/2007 | Sakai et al. |
| 2008/0051696 | A1 | 2/2008 | Curtin et al. |

FOREIGN PATENT DOCUMENTS

| | | | |
|---|---|---|---|
| EP | 0 003 914 A2 | 9/1979 | |
| EP | 0 064 393 A2 | 11/1982 | |
| JP | 56051237 | 5/1981 | |
| WO | WO 84/00885 | 3/1984 | |
| WO | WO 89/02756 | 4/1989 | |
| WO | WO 95/32736 A1 | 12/1995 | |
| WO | WO 97/33474 | 9/1997 | |
| WO | WO 98/00172 A2 | 1/1998 | |
| WO | WO 98/16171 | 4/1998 | |
| WO | WO 2004/009158 A2 | 1/2004 | |
| WO | WO 2004009158 A2 * | 1/2004 | ............... A61M 1/16 |
| WO | WO 2005/062973 A2 | 7/2005 | |
| WO | WO 2007/089855 A2 | 8/2007 | |
| WO | WO 2007/103411 A2 | 9/2007 | |

OTHER PUBLICATIONS

International Search Report from International Application No. PCT/US2008/009891, mailed on Dec. 15, 2008.
Colton, C.K., "Analysis of Membrane Processes for Blood Purification," *Blood Purification* 5:202-251 (1987).
Gura, V., et al., "Continuous Renal Replacement Therapy for Congestive Heart Failure: The Wearable Continuous Ultrafiltration System," *ASAIO Journal* 52(1):59-61 (2006).
Gura, V., et al., "Continuous Renal Replacement Therapy for End-Stage Renal Disease." In *Cardiovascular Disorders in Hemodialysis*, C. Ronco et al., eds. (Basel:Karger), vol. 149, pp. 325-333 (2005).
Lanza, R.P., et al., "Devices Implanted as AV Shunts." In *Pancreatic Islet Transplantation vol. III: Immunoisolation of Pancreatic Islets*, R.P. Lanza et al., eds. (R.G. Landes) 1994.
Lysaght, M.J., et al., "Filtration Rates and Pressure Driving Force in AV Filtration," *Blood Purification* 1:178-183 (1983).
Maki, T., et al., "Novel Delivery of Pancreatic Islet Cells to Treat Insulin-Dependent Diabetes Mellitus," *Clin. Pharmacokinet.* 28(6):471-482 (1995).
Shaldon, S., el al., "Continuous Ambulatory Hemofiltration," *Trans. Am. Soc. Artif. Intern. Organs XXVI*:210-212 (1980).
Chang, T.M.S., "A Comparison of Semipermeable Microcapsules and Standard Dialysers for Use in Separation," *Separation and Purification Methods*, 3(2): 245-262 (1974).
Chang, T.M.S., "Artificial Kidney, Artificial Liver, and Detoxifiers Based on Artificial Cells, Immobilized Proteins, and Immobilized Enzymes," In *Biomedical Applications of Immobilized Enzymes and Proteins*, T.M.S. Chang, eds. (NY: Plenum Press), pp. 281-295 (1977).
Chang, T.M.S., "Biodegradable Semipermeable Microcapsules Containing Enzymes, Hormones, Vaccines, and other Biologicals," *J. Bioengineering*, 1: 25-31 (1976).
Chang, T.M.S., "Encapsulation of Enzymes, Cell Contents, Cells, Vaccines, Antigens, Antiserum, Cofactors, Hormones and Proteins," In *Biomedical Applications of Immobilized Enzymes and Proteins*, T.M.S. Chang, eds. (NY: Plenum Press), pp. 69-90 (1977).
Chang, T.M.S., "Experimental Therapy Using Semipermeable Microcapsules Containing Enzymes and Other Biologically Active Material," In *Biomedical Applications of Immobilized Enzymes and Proteins*, T.M.S. Chang, eds. (NY: Plenum Press), pp. 147-162 (1977).
Chang, T.M.S., "Immobilization of Enzymes, Adsorbents, or Both within Semipermeable Microcapsules (Artificial Cells) for Clinical and Experimental Treatment of Metabolite-Related Disorders," *Birth Defects: Original Article Series*, IX(2): 66-76 (1973).
Chang, T.M.S., "Immobilized Enzymes and Their Biomedical Applications." In *Immobilized Enzymes, Antigens, Antibodies, and Peptides Preparation and Characterization*, H.H. Weetall, ed. (NY: Marcel Dekker, Inc.), pp. 245-292 (1975).
Baysal, S.H. and Uslan, A.H., "In Vitro Study of Urease/AlaDH Enzyme System Encapsulated into Human Erythrocytes and Research into its Medical Applications," *Art. Cells, Blood Subs., and Immob. Biotech.*, 30(1):71-77 (2002).
Blumenkrantz, M.J., et al., "Applications of the Redy® Sorbent System in Hemodialysis and Peritoneal Dialysis," *Artificial Organs*, 3(3):230-236 (1979).
Chang, T.M.S., "Artificial Cells with Emphasis on Cell Encapsulation of Genetically Engineered Cells," *Artificial Organs*, 22(11):958-965 (1998).
Diaz-Buxo, J.A., "Continuous-Flow Peritoneal Dialysis: Update," *Advances in Peritoneal Dialysis*, 20:18-22 (2004).
Gordon, A., et al., "Sorbent Regeneration of Peritoneal Dialysate: An Approach to Ambulatory Dialysis," *Journal of Dialysis*, 1(2):145-164 (1976-1977).
Lewin, A., "Sorbent Based Regenerative Peritoneal Dialysis System," *Dialysis & Transplantation*, 7(8):831, 833 (1978).
O'Loughlin, J.A., et al., "Degradation of Low Molecular Weight Uremic Solutes by Oral Delivery of Encapsulated Enzymes," *ASAIO Journal*, 50:253-260 (2004).
O'Loughlin, J.A., et al., "In Vivo and in Vitro Degradation of Urea and Uric Acid by Encapsulated Genetically Modified Microorganisms," *Tissue Engineering*, 10(9/10):1446-1455 (2004).
O'Loughlin, J.A., et al, "Oral Administration of Biochemically Active Microcapsules to Treat Uremia: New Insights into an Old Approach," *J. Biomater. Sci. Polymer Edn*, 15(11):1447-1461 (2004).
Prakash, S. and Chang, T.M.S., "Artificial Cells Containing Genetically Engineered *E. Coli* DH5 Cells for Urea and Ammonia Removal in Kidney and Liver Failure," *IEEE Engineering in Medicine and Biology $17^{th}$ Annual Conference*, vol. 2:1729-1730 (1995).
Roberts, M., et al., "Innovative Peritoneal Dialysis: Flow-Thru and Dialysate Regeneration," *ASAIO Journal*, 45:372-378 (1999).
Sparks, R.E., et al., "Removal of Waste Metabolites in Uremia by Microencapsulated Reactants," *Trans. Amer. Soc. Artif. Int. Organs, XV*:353-359 (1969).
Wolfe, E.A. and Chang, T.M.S., "Orally Ingested Microencapsulated Urease and an Adsorbent, Zirconium Phosphate, to Remove Urea in Kidney Failure," *The International Journal of Artificial Organs*, 10(4):269-274 (1987).
Non-Final Office Action for U.S. Appl. No. 12/610,969, "Portable Peritoneal Dialysis System", dated Mar. 25, 2013, consisting of 13 pages.
Notification of Transmittal of the International Search Report and the Written Opinion of the International Searching Authority, or the Declaration, from PCT/US2009/062967, mailed Jun. 25, 2010, 17 pages.
Notification Concerning Transmittal of International Preliminary Report on Patentability, from PCT/US2008/009891, mailed Mar. 4, 2010, 8 pages.

(56) References Cited

OTHER PUBLICATIONS

The State Intellectual Property Office of the People's Republic of China, First Office Action dated Dec. 12, 2010, Application No. 20078007691.6, English Translation.

Non-Final Office Action for U.S. Appl. No. 11/895,075 date mailed Nov. 18, 2010.

Final Office Action, U.S. Appl. No. 12/610,969, mail date Sep. 12, 2012.

Non-Final Office Action dated Jun. 28, 2013, U.S. Appl. No. 12/873,875.

Office Action, U.S. Appl. No. 12/610,969, date of mailing Apr. 24, 2012.

Roberts, M., et al., "Innovative Peritoneal Dialysis: Flow-Thru and Dialysate Regeneration," *ASAIO Journal*, pp. 372-378 (1999).

Raja, R. M., et al., "Recirculation Peritoneal Dialysis with Sorbent Redy Cartridge," *Nephron*, vol. 16, pp. 134-142 (1976).

Gordon, A., "Augmentation of Efficiency by Continuous Flow Sorbent Regeneration Peritoneal Dialysis," *Trans. Amer. Soc. Artif. Int. Organs*, vol. XXII, pp. 599-603 (1976).

Blumenkrantz, M. J., et al., "Development of a Sorbent Peritoneal Dialysate Regeneration System—A Progress Report," Proceedings of the Fifteenth Congress of the European Dialysis and Transplant Association, pp. 213-219 (1978).

Blumenkrantz, M. J., et al., "Applications of the Redy® Sorbent System to Hemodialysis and Peritoneal dialysis," Artificial Organs, vol. 3, (3), pp. 230-236 (1978).

ASN Program and Abstracts, *Journal of American Society of Nephrology*, vol. 2, (3), p. 367 (1991).

Non-Final Office Action dated Oct. 22, 2013 for U.S. Appl. No. 12/610,969.

\* cited by examiner

Design of Hollow Fiber Device
Urease + Ammonium Adsorbing Resin

FIG. 7

Summary of Wearable Peritoneal Dialysis System Component Specifications

| Molecule to be removed | Required removal quantity/day | Removed by which system component | Estimated component weight | Estimated component volume |
|---|---|---|---|---|
| Urea | 10 g/day | Oral capsules containing urease + ion exchange resin | | 240 ml |
| | 20 g/day | Urease + ion exchange resin | 220 g | 340 ml |
| | 20 g/day | Amberlyst 36 strong acid resin + weak acid resin | 150 g | 300 ml |
| Phosphate | 800 mg/day 25 mEq/day | Amberlite 96 anion exchange resin | 11 g | 25 ml |
| Sulfate | 50 mEq/day | Amberlite 96 anion exchange resin | 22 g | 50 ml |
| H+ | 60-70 mEq/day | Add base | | |
| Water | 1.5 L/day | 1 bag 4.25% glucose | N/A | N/A |
| Ca2+/Mg2+ | Avoid depletion by resin | Ion-selective membrane | N/A | N/A |
| Creatinine/ Other Organic | | Carbon | 50 g | 150 ml |

Size of Membrane Device

Assume: Q = 100 ml/min
Visc = 0.7 cP
Delta P max = 5 mmHg
Fiber ID – see table at right

| | Option A | Option B |
|---|---|---|
| Fiber ID | 230 um | 300 um |
| L | 8 cm | 16 cm |
| Area, cm² (m²) | 1178 (0.1) | 2124 (0.2) |
| N fibers | 2039 | 1408 |
| Volume (cm³) | 6.8 | 15.9 |

WEARABLE KIDNEY

BACKGROUND OF THE INVENTION

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites including urea, creatinine and uric acid accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysate. The waste and toxins dialyze out of the blood through the semi-permeable membrane into the dialysate, which is then discarded. Hemodialysis treatment typically lasts several hours and must be performed under medical supervision three or four times a week, requirements that significantly decrease a patient's autonomy and quality of life. Also, since hemodialysis is performed periodically instead of continuously, the patient's condition and general well-being tend to be poor both immediately before (when toxin levels are high) and after (when electrolytes are imbalanced) hemodialysis, resulting in the patient having symptoms that range from nausea and vomiting to edema.

Peritoneal dialysis is another type of dialysis treatment used to replace kidney function in which sterile, pyrogen-free dialysis solution is infused into the patient's peritoneal cavity. The peritoneal membrane serves as a natural dialyzer and toxic uremic waste metabolites and various ions diffuse from the patient's bloodstream across the membrane into the dialysis solution via an osmotic gradient. The dialysis solution is removed, discarded and replaced with fresh dialysis solution on a semi-continuous or continuous basis. Although not all peritoneal dialysis systems require medical supervision in a treatment center, draining, discarding and replacing the large volumes of solution needed for peritoneal dialysis is still inconvenient, unwieldy and expensive.

To address this problem, devices have been designed that reconstitute used dialysate from hemodialysis and/or peritoneal dialysis as opposed to discarding it. The solution can be regenerated in a machine employing a device that eliminates urea from the solution. For example, the original Redy® (REcirculating DYalysis) Sorbent System (Blumenkrantz et al., *Artif Organs* 3(3):230-236, 1978) consists of a sorbent cartridge having five layers through which dialysate solution containing uremic waste metabolites flows in order to be regenerated. The spent dialysate flows through a purification layer that removes heavy metals (i.e., copper and lead) and oxidants (i.e., chlorine and chloramine), an aluminum oxide layer bound to urease which degrades the urea in the dialysate into ammonium carbonate, a zirconium phosphate layer that adsorbs the ammonium ions produced from urea degradation along with other cations (i.e., potassium, magnesium and calcium), a hydrated zirconium oxide layer that exchanges phosphate and other anions (i.e., fluoride) for acetate and an activated carbon layer that absorbs other organic compounds (i.e., creatinine and uric acid).

Typically, the ion exchange resins used in devices such as the Redy® Sorbent System absorb not only the urea degradation products, but also essential ions like calcium and magnesium that have diffused into the peritoneal dialysis solution. These ions must then be rapidly replaced in the patient; however, there currently is no easy or convenient mechanism to do so. Further, although hemodialysis and peritoneal dialysis dialysate can be regenerated, no device has yet been devised that both operates continuously, clears uremic waste metabolites effectively and is small enough and/or weighs little enough to actually be comfortably worn by a patient at all times.

There is a need for a dialysis device that is safe and effective and that significantly improves a patient's quality of life over current devices and methods. What is required is a dialysis device that operates regularly enough such that the patient does not feel unwell for significant periods of time and one that does not consume large blocks of the patient's time, require medical supervision, require volumes of dialysate so large that the patient must practicably remain stationary, nor remove essential ions and minerals from the patient that then must be replaced externally. It would also be advantageous for the system to be safe enough for a patient to wear continuously and perform normal activities with little worry; that is, a system that does not involve the filtration of blood (e.g., hemodialysis), as a malfunction or disconnect within the blood circulation system could easily occur and result in rapid blood loss and death. Thus, there would be a great benefit to a dialysis system that truly allows a patient to function independently. Hence, a peritoneal dialysis device that is small enough to be comfortably worn by a patient continuously during daily activities and contains a regenerative device that is capable of reconstituting the dialysis solution without also removing essential ions from the patient.

SUMMARY OF THE INVENTION

The present invention provides a peritoneal dialysis device that is truly wearable—that is, a device that can be comfortably worn by a patient continuously, 24 hours a day, 7 days a week. The dialysis device, small in size and unobtrusive, recirculates peritoneal dialysis solution that is regenerated using a replaceable cartridge that does not absorb essential ions like calcium and magnesium from the patient. The dialysis treatment can be continuous or semi-continuous.

Accordingly, the invention relates to a wearable peritoneal dialysis system. In one embodiment, the system comprises a closed fluid system loop that circulates a volume of peritoneal dialysis solution into and out of a patient's peritoneal cavity through an access port. Attached to the fluid system loop of the wearable peritoneal dialysis system are: at least one pump for moving the peritoneal dialysis solution into and out of the patient's peritoneal cavity, a replaceable drain container for removing excess fluid resulting from osmosis of the fluid from the patient's body into the peritoneal dialysis solution, a filter for removing particulates and debris from the peritoneal dialysis solution and a replaceable cartridge for regenerating the peritoneal dialysis solution attached to the fluid system loop, the replaceable cartridge having an urea removal layer that rejects calcium and magnesium so that they are retained in the peritoneal dialysis solution and thus, in the patient.

The wearable peritoneal dialysis system can be used in conjunction with a source of one or more enzymes capable of degrading uremic waste metabolites, the source of the one or more enzymes orally administered to a patient such that the uremic waste metabolites needing to be cleared by the wearable peritoneal dialysis device may be simplified or reduced in amount. The source of one or more enzymes can be enzymes like urease or creatininase, or cells that naturally express or are engineered to express the enzymes. In one embodiment, the administered enzymes are encapsulated. In a particular embodiment, the enzymes are administered with an encapsulated sorbent that adsorbs the urea degradation products or, alternatively, the two are encapsulated together. In another embodiment, the encapsulation surrounding the sorbent and/or enzymes rejects calcium and magnesium ions to prevent their binding to the sorbent.

In another embodiment, the wearable peritoneal dialysis system can further comprise a mix container attached to the fluid system loop to re-mix the regenerated peritoneal dialysis solution with additional glucose, as needed, to achieve the required peritoneal osmotic flows. In yet another embodiment the wearable peritoneal dialysis device further comprises a filter attached to the fluid system loop that removes bacterial contamination from the regenerated peritoneal dialysis solution. A microprocessor can be in communication with the fluid system loop components to control the pump flow rates and the timing and sequencing of the components of the dialysis system, a microprocessor that can also be designed to be controlled externally as well.

The invention also relates to a replaceable cartridge that regenerates peritoneal dialysis fluid, the replaceable cartridge comprising a purification layer, a urea removal layer that rejects calcium and magnesium ions and an ion exchange layer. The purification layer removes heavy metals, oxidants and other uremic waste metabolites from the peritoneal dialysis fluid and, in one embodiment, is comprised of activated carbon. The ion exchange layer removes phosphate and sulfate from the peritoneal dialysis fluid and can consist of a polymeric phosphate binder or an ion exchange resin.

In one embodiment, the urea removal layer is comprised of a strong acid cation resin that adsorbs the urea and a weak base anion resin that adsorbs the counter ions released by the urea adsorption and hollow fibers through which the peritoneal dialysis solution flows, the hollow fibers coated with a material through which the urea can pass but calcium and magnesium ions can not. In another embodiment, the urea removal layer is comprised of an urea-degrading enzyme, like urease, that degrades the urea, an ion exchange sorbent that adsorbs the urea degradation products and hollow fibers that again, via a coating with an ion-rejecting material, allows urea to flow through but rejects calcium and magnesium ions. Alternatively, the hollow fibers can be comprised of an ion-selective nanofiltration membrane that rejects divalent cations. In another embodiment, instead of containing hollow fibers, the strong acid and weak base resins or the enzyme and ion exchange sorbent can be encapsulated, the encapsulation material allowing the passage of the urea through it, but rejecting calcium and magnesium ions. The ion-rejecting material coating the hollow fibers or encapsulating the resins can be materials that reject calcium and magnesium ions by electrostatic repulsion, hydrophobicity or size exclusion. Thus, calcium and magnesium ions are retained in the peritoneal dialysis solution and therefore, do not have to be replaced in the patient.

The invention further relates to a method of removing uremic waste metabolites from a patient using the wearable peritoneal dialysis system, the method comprising pumping a volume of peritoneal dialysis solution through an access port into a patient's peritoneal cavity such that the patient's uremic waste metabolites diffuse across the peritoneal membrane into the peritoneal dialysis solution; pumping the dialysis solution containing uremic waste metabolites out of the patient and into the system; draining excess fluid into a replaceable drain container; filtering particulates and debris from the peritoneal dialysis solution; regenerating the peritoneal dialysis solution containing uremic waste metabolites using a replaceable cartridge containing an urea removal layer that rejects calcium and magnesium ions and returning the regenerated peritoneal dialysis solution to the patient's peritoneal cavity. The method further comprises orally administering to a patient a source of one or more enzymes capable of degrading uremic waste metabolites such that the load of uremic waste metabolites is reduced and/or the degraded metabolites are more easily removed from the patient by the wearable peritoneal dialysis system and from the patient's intestines.

Unlike dialysis systems to date, the wearable peritoneal dialysis system of the invention provides for a dialysis device that allows the patient to maintain a relatively normal, active lifestyle. Hence, the wearable peritoneal dialysis system is far safer than wearable hemodialysis and/or filtration systems which have a very real risk of line break or disconnect from the patient that can lead to rapid and fatal blood loss. Due to the regeneration of the peritoneal dialysis solution, only a small volume of solution needs to be circulated in the wearable peritoneal dialysis system which allows the system to be small and lightweight and thus, comfortable to wear overall. As the wearable peritoneal dialysis system is able to operate continuously through regeneration of the peritoneal dialysis solution, it dramatically improves a patient's overall well-being and quality of life, freeing the patient from dialysis systems that are labor-intensive, time-consuming and/or require medical supervision for operation. Regeneration of the peritoneal dialysis solution in a continuously wearable peritoneal dialysis system also means that patients do not have to frequently connect and disconnect fluid connectors to the peritoneum, a requirement in conventional peritoneal dialysis that frequently introduces infection at the connection site. Moreover, the wearable peritoneal dialysis system regenerates the peritoneal dialysis solution without removing essential ions from the solution and, ultimately, from the patient's body. This is most advantageous as currently, these essential ions can not be replaced in the patient as quickly or effectively as needed.

BRIEF DESCRIPTION OF THE DRAWINGS

FIG. 7 is a table outlining specifications for a fluid system loop and replaceable cartridge of the wearable peritoneal dialysis system.

DETAILED DESCRIPTION OF THE INVENTION

The present invention generally relates to a continuous, wearable peritoneal dialysis system that removes uremic waste metabolites from a patient suffering from, a disorder associated with the accumulation of uremic toxins (e.g., chronic kidney failure). The system can be used to treat a disorder like, for example, renal disease, including early renal disease, renal dysfunction or renal failure (e.g., end stage renal disease). As used herein, the term "uremic waste metabolites" refers to compounds, such as those containing nitrogen, produced by the body as waste products and includes compounds like urea, uric acid, creatinine and β2-microglobulin. Renal failure or dysfunction leads to uremic toxicity which occurs when the levels of uremic waste metabolites in a patient are elevated compared to the levels of the toxins in individuals with normal renal function.

Thus, the present invention relates to a wearable peritoneal dialysis system that, unlike previous systems and devices, is small enough in size to be wearable without significant burden to a patient 24 hours a day, 7 days a week. The peritoneal dialysis can be performed continuously or semi-continuously as the system contains a replaceable cartridge that regenerates the peritoneal dialysis solution that is then recirculated in the system. Preferably, the wearable peritoneal dialysis system is used in conjunction with a source of one or more enzymes that degrade uremic waste metabolites, thus decreasing or reducing the complexity of the toxins needing to be eliminated by the wearable device, which in turn allows the device to be small and unobtrusive. For example, the wearable peritoneal dialysis system is envisioned to be of size and dimensions similar to an insulin pump (e.g., Mini-Med Paradigm® insulin pump, Medtronic, Inc.).

The wearable peritoneal dialysis system is comprised of one or more access ports coupled to a component to provide inflow to and outflow from the patient's peritoneal cavity, where the component can include medically appropriate plastic tubing, a double lumen catheter or two single lumen catheters. The wearable peritoneal dialysis system also contains a volume of peritoneal dialysis solution that is infused into and out of the patient's peritoneal cavity such that the peritoneal dialysis solution removes uremic waste metabolites that diffuse through the peritoneal membrane into the peritoneal dialysis solution. Preferably, the system will continuously recirculate for maximum mass transport of the peritoneal dialysis solution, although periodic dwell times could be advantageous. Any peritoneal dialysis solution can be used (e.g., Delflex), these solutions being commercially available (e.g., Fresenius Medical Care North America) and well-known in the art. A volume of about 0.5 to 2 liters of peritoneal dialysis solution can be introduced into the wearable peritoneal dialysis system and it is preferable that about 2 liters of the solution be infused.

Figure 1:
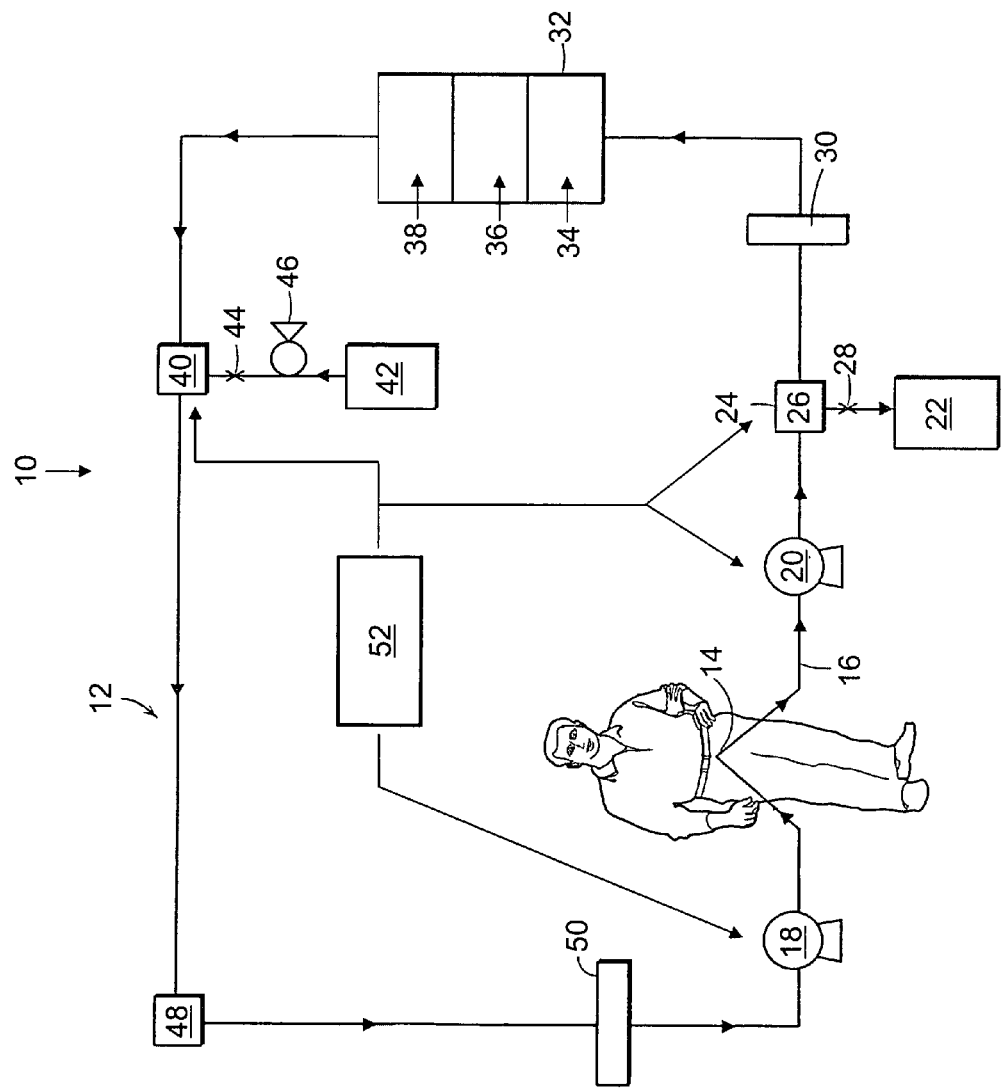
FIG. 1 is a schematic illustrating the fluid system loop of a wearable peritoneal dialysis system according to the invention.

Turning to FIG. 1, a wearable peritoneal dialysis system 10 is comprised of a closed, fluid system loop 12 that circulates the peritoneal dialysis solution from the patient through access port 14, throughout the components of the fluid system loop 12 along fluid path 16 and back to the patient. In one embodiment, there is at least one pump attached to the fluid system loop to both infuse peritoneal dialysis solution into the patient's peritoneal cavity and move the peritoneal dialysis solution containing uremic waste metabolites out of the peritoneal cavity and into the fluid system loop 12. There can be one, and preferably two or more such pumps throughout fluid system loop to aid in the circulation of the peritoneal dialysis solution. As shown in FIG. 1, the peritoneal dialysis solution is infused into the patient via inflow pump 18 and the peritoneal dialysis solution, containing uremic waste metabolites and other ions that have diffused into the peritoneal dialysis solution through the peritoneal membrane, is moved out of the patient via out flow pump 20. The one or more pumps can be any small and/or miniature pumps known in the art (e.g., Scientifics® Miniature Pump). In one embodiment, the peritoneal dialysis solution is pumped through the fluid loop system at a rate of about 50 to 500 milliliters/minute (mL/min).

Also attached to fluid system loop 12 is a replaceable drain container 22 which drains excess fluid 24 that has been added to the peritoneal dialysis solution through osmosis from the patient's body. The wearable peritoneal dialysis system 10 can be further comprised of a three-way valve 26 attached to the fluid system loop 12 that is an outlet to the replaceable drain container 22 and an on-off switch 28 between the three-way valve 26 and the replaceable drain container 22 which regulates the drainage of excess fluid 24. The drainage of the excess fluid can occur at a rate as determined to be appropriate by the skilled artisan and preferably at a rate of about 0.5 to 2 liters per 24 hour period. The drainage of excess fluid can occur periodically with dialysis being continuous, where the patient periodically empties the excess fluid from the replaceable drain container. Alternatively, the dialysis can be performed for a specified period of time and the drainage of excess fluid can occur during a period of time subsequent to the dialysis. For example, the dialysis can be performed for 20 hours of the day and the drainage of excess fluid for 4 hours of the day, the drainage, in this case, preferably occurring while the patient is asleep.

The wearable peritoneal dialysis system 10 can also be comprised of a filter 30 attached to the fluid system loop 12 that removes particulates, debris and, if desired, some proteins from the peritoneal dialysis solution containing uremic waste metabolites. Numerous filters of the appropriate size and molecular weight cut off (MWCO) can be used and are commercially available (e.g., Millipore). Filter 30 can be comprised of any effective membranous material, and typically would be made up of materials like cellulose, nylon, polyvinylidene fluoride, polysulfone, polyethersulfone and polypropylene. Preferably, filter 30 would be easily replaceable and/or disposable such that the filter could be changed when saturated with particulates and/or debris, for example. In one embodiment of the invention, the filter is no larger than the replaceable cartridge, such that it can be worn, and has a MWCO of less than 60 kDa. The peritoneal dialysis solution which is circulated through fluid system loop 12 continuously, is regenerated by a replaceable cartridge 32 attached to the fluid system loop. The replaceable cartridge is made up of three layers: a purification layer 34 that removes heavy metals, oxidants and other uremic waste metabolites from the peritoneal dialysis solution, a urea removal layer 36 that eliminates urea from the solution but rejects calcium and magnesium so that the ions are retained in the solution and an ion exchange layer 38 that removes phosphate and sulfate from the peritoneal dialysis solution (see also FIG. 2). The components of the replaceable cartridge of the invention are reduced in size compared to existing devices in order to allow the device to be easily worn on the patient's body. Preferably, the dimensions of the replaceable cartridge would be as small as possible to be the least obtrusive. Advantageously, the cartridge and its components can be replaced, thus when the contents of the various layers become saturated by the particular agents each layer binds and/or eliminates, the layer/section of the cartridge and/or the entire cartridge itself can be removed and easily replaced.

Accordingly, in the replaceable cartridge, the peritoneal dialysis solution first flows through purification layer 34 which typically would be comprised of activated carbon/charcoal. The solution next flows through urea removal layer 36 which is made up of urea removal components and a composition that rejects calcium and magnesium ions. As used herein, the term "urea removal components" refers to components of the replaceable cartridge that eliminate urea by adsorbing (e.g., a strong acid cation resin) or breaking down (e.g., an urea-degrading enzyme) the urea and binding and/or removing (e.g., weak base resin or ion exchange sorbent) the byproducts of the urea elimination reactions. The urea removal layer 36 is also comprised of a composition able to reject the calcium and magnesium ions that have diffused from the patient into the peritoneal dialysis solution in the patient's peritoneal cavity via a concentration gradient. The calcium and magnesium rejecting composition can be comprised of ion-selective elements that prevent calcium and magnesium from being removed from the peritoneal dialysis solution and can include hollow fibers made of an ion-selective nanofiltration membrane, hollow fibers coated with an ion-rejecting material or an encapsulation surrounding the urea removal components.

Figure 3:
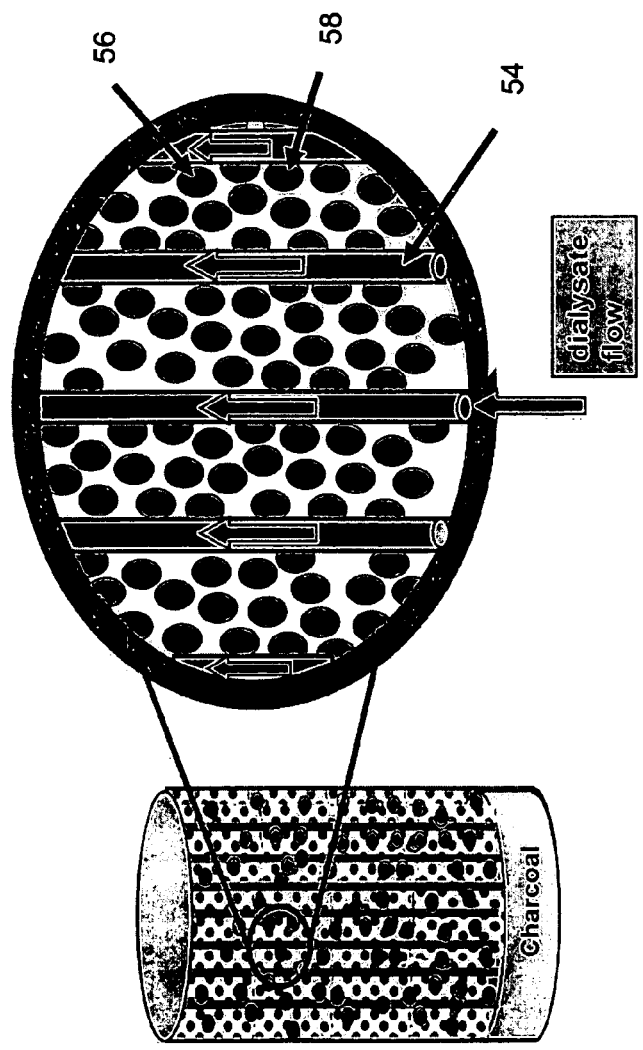
FIG. 3 is a drawing illustrating a hollow fiber device in the urea removal layer of a replaceable cartridge containing a strong acid adsorbent to remove urea from the peritoneal dialysis solution.

Thus, in one embodiment, the urea removal layer is made up of a strong acid cation exchange resin (e.g., Amberlyst™ 36) and a weak base resin (e.g., Amberlite™ 96) or a dual-property resin (e.g., Bio-Rad AG 51-X8) to remove urea (see also FIG. 3). As used herein, the term "dual-property resin" refers to an ion exchange resin that can act as both a strong acid cation exchange and a weak base anion exchange resin. In addition to the strong acid and weak base resin(s), the urea removal layer can also be comprised of hollow fibers 54 made of an ion-selective nanofiltration membrane (available from, e.g., Amerida, Koch, BE, Hoechst and Dow) or coated with a divalent cation-rejecting material (e.g., cellulose acetate) that prevents calcium and magnesium diffusion from the peritoneal dialysis solution. Alternatively, in another embodiment, the ion-rejecting component can be an ion-selective encapsulation (e.g., polysulfone) that surrounds the strong and weak base resins or the dual-property resin, the encapsulation allowing the urea through but repelling divalent cations. In yet another embodiment, the urea removal layer can be comprised of a urea-degradation enzyme (e.g., urease) and an ion exchange sorbent (e.g., zirconium phosphate), the enzyme and sorbent encapsulated with an ion-rejecting material (e.g., cellulose acetate). In this embodiment also the composition rejecting the calcium and magnesium ions can alternatively be comprised of hollow fibers made of an ion-selective nanofiltration membrane or hollow fibers coated with an ion-rejecting material. The material coating the hollow fibers or surrounding the urea removal components would most likely be positively charged, causing it to reject similarly charged ions like calcium and magnesium.

To complete the regeneration of the peritoneal dialysis solution, the solution then flows through ion exchange layer 38 that removes phosphate and sulfate from the peritoneal dialysis solution. The ion-exchange layer can be comprised of either a polymeric phosphate binder (e.g., Renagel®) or an ion exchange sorbent (e.g., zirconium oxide). The replaceable cartridge of the wearable peritoneal dialysis system preferably removes phosphate from the patient at a rate of about 8 to 12 milliliters/minute (mL/min) and clears urea from the patient at a rate of about 10 to 15 mL/min. Sulfate is preferably cleared from the patient at a rate of about 50 milliequivalents (mEq) per 24 hours and, similarly, hydrogen ions are cleared from the patient at a rate of about 60 to 70 mEq in a 24 hour period. The regeneration of the peritoneal dialysis solution in the replaceable cartridge for recirculation in the wearable peritoneal dialysis system allows a small volume of the solution to be used in the system such that it is light and compact enough to be worn by a patient with ease.

The wearable peritoneal dialysis system 10 can be further comprised of a mix container 42 attached to the fluid system loop 12 so that glucose can be added, as necessary, to maintain the correct osmotic flow in the peritoneum. Accordingly, the wearable peritoneal dialysis system can be further comprised of a three-way valve 40 attached to the fluid system loop 12 that serves as an outlet to the mix container 42; an on-off flow switch 44 between the three-way valve 40 and the mix container 42 that regulates flow of the regenerated peritoneal dialysis solution into the container; and a flow pump 46 between the on-off switch 44 and the mix container 42 that contains a glucose solution, the pump serving to infuse the glucose solution into the mix container with the regenerated peritoneal dialysis solution. Preferably, the glucose is added at a concentration of about 4.25 percent. In addition, the wearable peritoneal dialysis system can contain a three-way valve 48 that connects the flow of the re-mixed and regenerated peritoneal dialysis solution to an initial priming point of the fluid system loop.

A filter 50 able to remove bacterial contamination from the regenerated peritoneal dialysis solution can also be attached to the fluid system loop 12 of the wearable dialysis system. Filters that remove and/or eliminate bacteria are known in the art and are commercially available (e.g., JMC, A-M Systems, Millipore and Direct Med., Inc). The filter could be comprised of any material (e.g., cellulose, polyethersulfone, nylon, polyester or polystyrene) appropriate to exclude and/or sequester bacteria from the solution based on size and/or chemical or biological properties of the bacteria and would only need to be of the correct shape and size to fit appropriately in the wearable peritoneal dialysis system. Thus, the filter is envisioned to be no larger than the replaceable cartridge and have a filtration cut-off of about 0.01 microns or less. Bacterial filter 50 would, preferably, also be removable and/or replaceable.

As a means of controlling the components of the wearable peritoneal dialysis system, in one embodiment of the invention microprocessor 52 can be in communication with the components of the system (e.g., inflow pump 18, out flow pump 20, three-way valve 26 and/or three way valve 40). Microprocessor 52 can control, alter and adjust the pump flow rates and the timing and sequencing of the components of the dialysis system in response to pre-programmed instructions or according to the patient's needs as determined by the skilled clinician. The wearable peritoneal dialysis system 10 could also contain sensors able to measure sulfate concentrations such that microprocessor 52 can calculate relevant biostatistics (e.g., level of uremic waste metabolites removed or ions absorbed) and be programmed to adjust accordingly the pump speed, for example, such that the patient receives the most efficacious treatment. Microprocessor 52 is preferably located within the unit housing the wearable peritoneal dialysis system 10 itself to direct and coordinate the components of the dialysis system. There could also be an external, wireless control system (e.g., another microprocessor) that could, as needed, direct and adjust the wearable peritoneal dialysis system through the microprocessor 52 that is within the wearable dialysis system unit itself.

Figure 6:
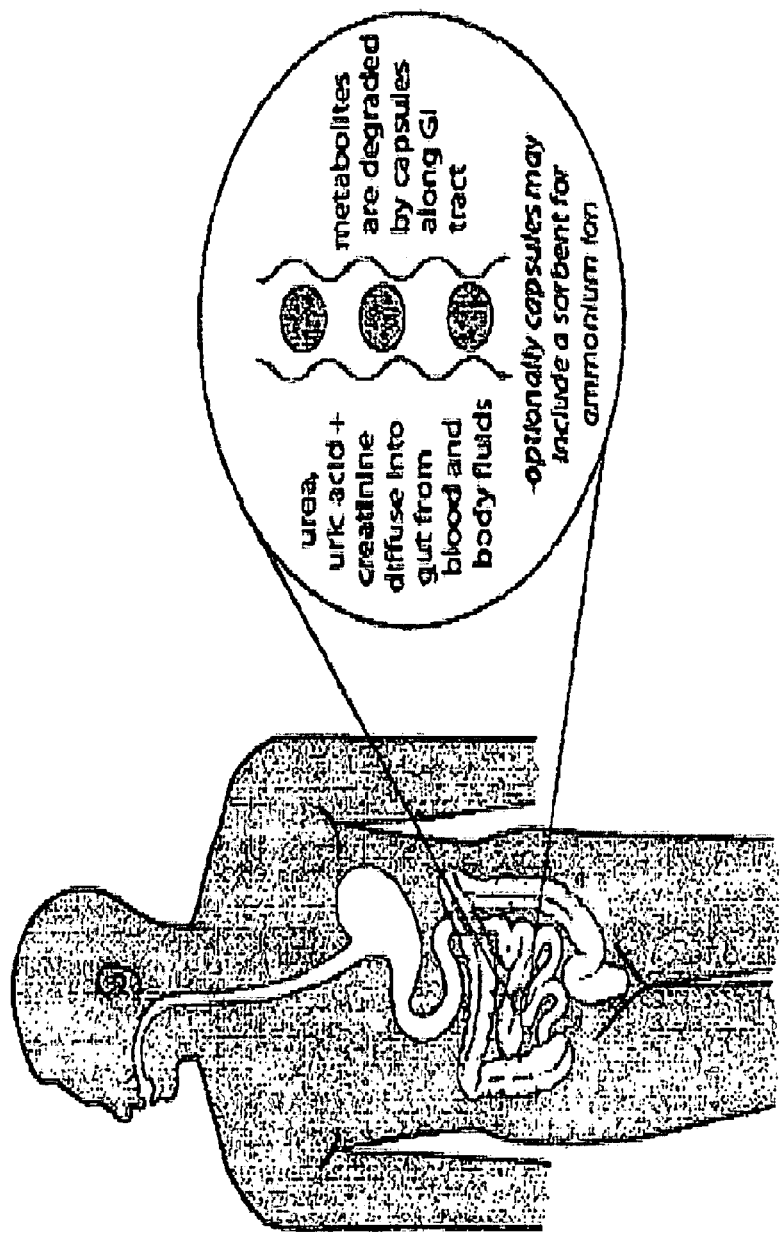
FIG. 6 is a drawing illustrating a patient who has orally ingested encapsulated enzymes that degrade uremic waste metabolites.

The wearable peritoneal dialysis system can be used in conjunction with a source of one or more enzymes capable of degrading uremic waste metabolites as described in O'Loughlin et al., *Tissue Eng.* 10: 1446-1455, 2004 and O'Loughlin et al. U.S. 2005/0123529, the entire teachings of which are herein incorporated by reference. O'Loughlin et al. discloses methods to reduce the concentration of uremic toxins in vivo by either orally delivering to a patient with renal dysfunction enzymes, generally encapsulated, or organisms and/or cells capable of eliminating and/or degrading uremic toxins. FIG. 6 shows a patient who has orally ingested encapsulated enzymes that are able to degrade uremic waste metabolites, in which the metabolites are degraded by the enzymes in the gastrointestinal tract. Oral administration of the enzymes in conjunction with the use of the peritoneal dialysis system decreases the load of uremic waste metabolites needing to be removed from the patient by the wearable peritoneal dialysis system, allowing the system to use less peritoneal dialysis solution and, consequently, be small enough to be wearable. Further, the orally ingested enzymes, by breaking down the uremic waste metabolites, allow the smaller degradation products to be more easily removed by the wearable peritoneal dialysis system and/or the patient's intestines. The source of enzymes can include enzymes known to degrade uremic waste metabolites like uricase, urease or creatininase, or any other suitable enzymes known to one having skill in the art, or a cell naturally occurring or genetically engineered that degrades uremic waste metabolites through the expression of one or more degradation enzymes or proteins that regulate the one or more enzymes' expression or activity.

The enzymes can be administered by any suitable method including direct administration of the enzymes (e.g., as a pharmaceutical composition in an appropriate carrier), in an encapsulation (e.g., a capsule, sustained release pill or liposome) or direct administration of a cell that expresses the enzymes (e.g., a microbial, yeast or mammalian cell in a suitable carrier). In a preferred embodiment of the invention, the enzymes are encapsulated in a material like silicone, polystyrene, alginate, other polymers, cellulose, any combination of the aforementioned materials or any other medically appropriate, non-toxic material known to those of skill in the art. The encapsulation surrounding the sorbent and/or enzymes can also reject calcium and magnesium ions such that these ions are not adsorbed by the sorbent and removed from the patient's body. A single enzyme can be encapsulated or one or more enzymes can be encapsulated so long as the one or more enzymes are able to break down urea. Degraded uremic waste metabolites can be delivered to and eliminated by the intestines. The enzymes can be administered with a sorbent (i.e., an ion exchange sorbent like zirconium phosphate) that can adsorb the urea degradation products. The sorbent can be encapsulated with, or in a separate encapsulation from, the one or more enzymes. Generally, the sorbent would also be orally administered. In another embodiment, if the uremic waste metabolites are degraded by a cell (e.g., a microbe), the cell itself may sequester the degradation products, which are then eliminated from the patient's body with the cell.

The amount of enzymes or cells administered to a patient to sufficiently decrease the load of uremic waste metabolites can be determined by one with skill in the art and will vary from patient to patient. The dosage will depend on the severity of the renal failure or dysfunction, the patient's age, body weight, overall well-being and the particular agent chosen under the specific conditions of administration. Preferably, the dosage does not have a negative effect on the patient. The source of the one or more enzymes can be administered once or several times during a 24 hour period, the schedule of administration dependent on the patient's need to meet a particular level of clearance of uremic waste metabolites and the patient's tolerance as determined by the skilled clinician and based on experimental models and clinical results.

Figure 2:
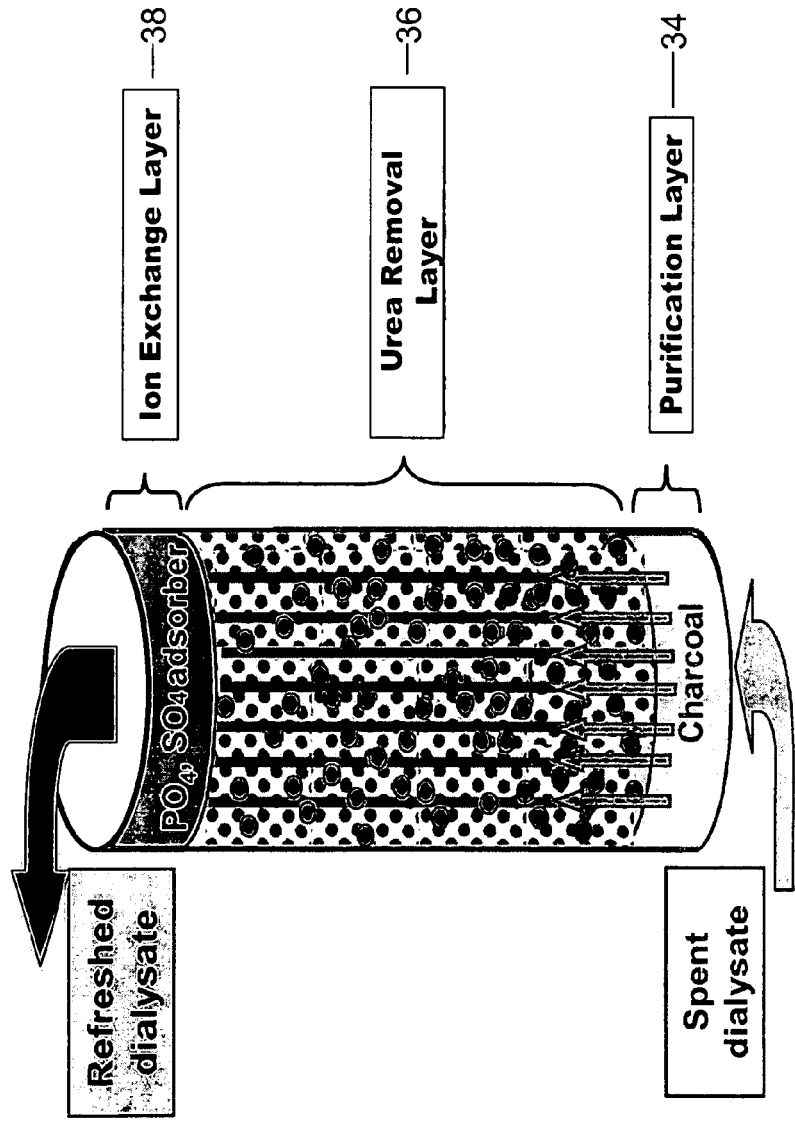
FIG. 2 is a drawing illustrating a replaceable cartridge of a wearable peritoneal dialysis system according to the invention.

The present invention further relates to a replaceable cartridge for use in the system that regenerates the peritoneal dialysis fluid in the system without absorbing calcium and magnesium ions that, through a concentration gradient, have diffused from the patient's body into the peritoneal dialysis solution in the peritoneum. The replaceable cartridge for use in the wearable peritoneal dialysis system contains a purification layer, urea removal layer that rejects the calcium and magnesium ions in the peritoneal dialysis solution and an ion exchange layer. In one embodiment, each layer and/or section of the cartridge can be removed and thus, replaced when desirable, e.g., when the layer/component wears out and/or becomes saturated by the elements it eliminates from the peritoneal dialysis solution. In addition, the entire cartridge can be replaceable and thus removed from the wearable peritoneal dialysis system when there is a decrease in the regeneration efficiency of the cartridge (e.g., through layer saturation) or the cartridge becomes worn or damaged, for instance. Turning to FIG. 2, peritoneal dialysis solution enters the replaceable cartridge, first encountering purification layer 34 which, like the purification layer of the device of the Redy® URS System (Renal Solutions, Inc.), removes heavy metals (e.g., lead, mercury, arsenic, cadmium, chromium and thallium), oxidants (e.g., chlorine and chloramine) and other uremic waste metabolites (e.g., creatinine and uric acid) using activated carbon, typically charcoal.

The peritoneal dialysis solution next flows through urea removal layer 36 which can, in a number of ways, eliminate urea from the solution while allowing essential ions to be retained in it. In one embodiment, the layer is comprised of a strong acid cation resin, a weak base anion resin and a composition that rejects calcium and magnesium ions. The strong acid and weak base resins can be separate resins, or one dual-property mixed bead resin. Strong acid cation resins are well-known in the art (e.g., Amberlyst™ 36, 131, 15, 31, 35, 39, 40 and 70; DOWEX™ C, C-10, C-350, C-400, 650C(H), 575C NG(H), N406, G-26(H), HCR-S/S, HCR-W2, HGR-W2, MSC, 88, M-31, MP-525C(H), DR-2030, MC-575(H), MSC-1, 88 MB and 88; Rexyn™ resins) and are commercially available (e.g., Rohm and Haas, Dow and Fisher-Scientific). Positive counter ions (e.g., hydrogen and sodium) are released through the process of urea adsorption to the strong acid cation resin and these ions are bound by weak base resin, to rebalance the pH of the peritoneal dialysis solution. The weak base resin can be any appropriate polyamine ion (anion) exchange resin available or its acid salt complex including: DOWEX 66, 77, WBA, WBA-2, WB-500, M-43, XUS 43594.00, and XUS 43568.00, Amberlite IRA67, IRA743, IRA96 and others, these resins available from Dow and Rohm and Haas, for example. As shown in FIG. 3, the strong acid and weak base resins are distinct and the composition that rejects calcium and magnesium are hollow fibers, the hollow fibers either coated with a material that rejects the ions or comprised of an ion-selective nanofiltration membrane. The peritoneal dialysis solution travels through hollow fibers 54, the urea passing through hollow fibers 54 and adsorbed by strong acid cation resin 56. By rejecting calcium and magnesium ions, the hollow fibers allow these ions to be retained in the peritoneal dialysis solution that is returned to the patient. Advantageously, as urea is not broken down, urea degradation products are not formed (e.g., ammonium carbonate) and thus, do not have to also be removed from the peritoneal dialysis solution.

Figure 4:
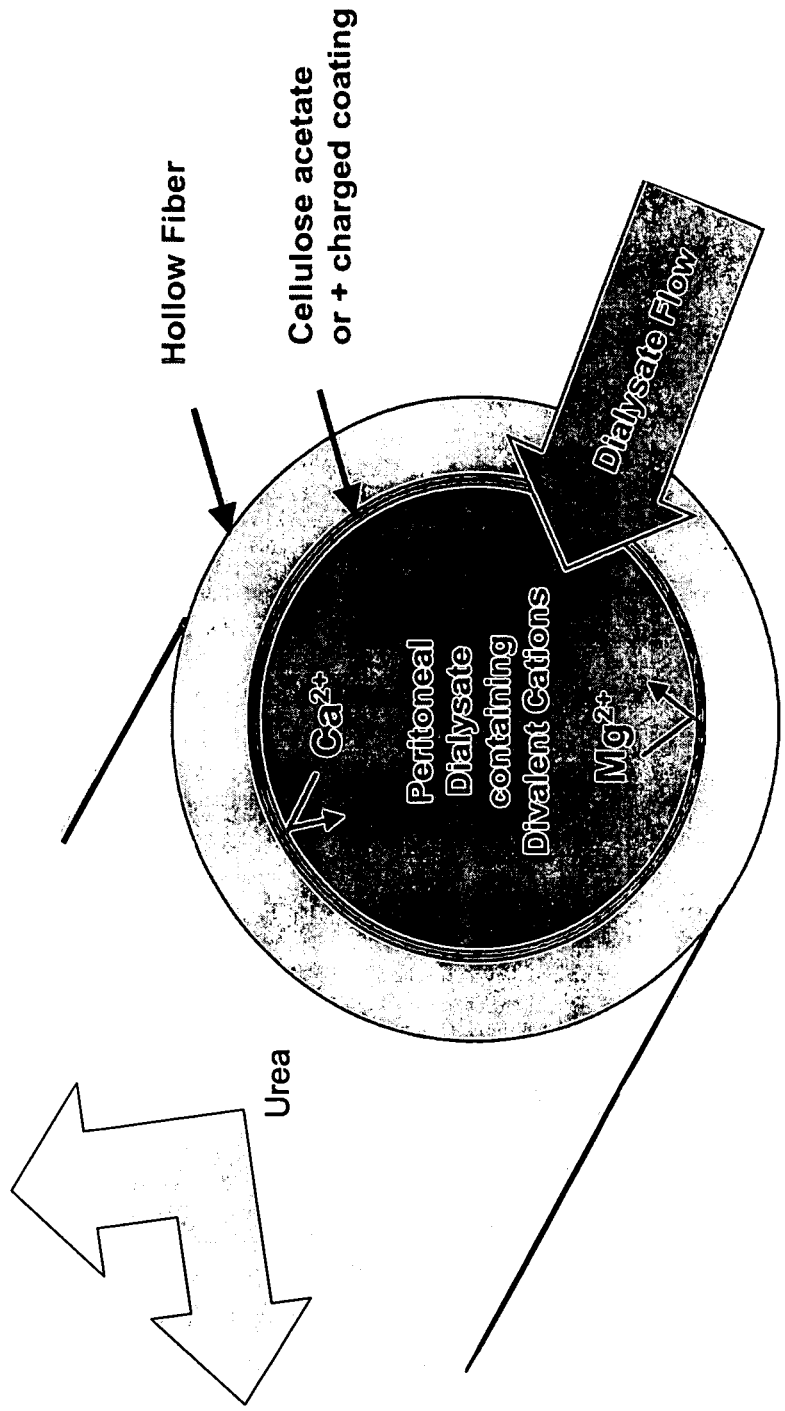
FIG. 4 is a drawing illustrating a hollow fiber in a replaceable cartridge that has a coating that rejects calcium and magnesium ions.

An embodiment in which the hollow fibers are coated with an ion-rejecting material is depicted in FIG. 4. The hollow fibers are coated with a material which, through a water-purification like mechanism, allows the urea through but rejects positively charged ions such as calcium and magnesium. The material coating the hollow fibers can be any known to one of skill in the art (e.g., fatty acids or polymer chains like polysulfone) that can effectively reject calcium and magnesium and therefore retain the ions in peritoneal dialysis solution. Generally, to have this effect the material itself would be positively charged and, in one embodiment, the material used to coat the hollow fibers is cellulose acetate, in particular, cellulose triacetate. The hollow fibers that are to be coated are commercially available (e.g., Fresenius Medical Care North America) and, for use in the invention, need only be able to be coated with the desired ion-rejecting material available to one having skill in the art. Alternatively, the hollow fibers can be comprised of an ion-selective nanofiltration membrane, such membranes also commercially available from a number of sources (e.g., Amerida, Koch, GE, Hoechst and Dow). These membranes have pores sizes that prevent ionic substances from diffusing through the membrane. For example, there are nanofiltration membranes that have an ability to reject ions with more than one negative charge (e.g., sulfate and phosphate) while allowing single-charged ions to pass through, with the converse also being the case. In either case, the hollow fiber devices are available in a variety of dimensions and need only be small enough to fit in the replaceable cartridge, which is sized to be comfortably worn.

In yet another embodiment, the strong acid and weak base resins or dual-property resin can themselves be encapsulated by a material through which urea can pass, but calcium and magnesium can not. Hence, the peritoneal dialysis solution would flow into the urea removal layer comprised of the encapsulated resin(s) and the urea in the peritoneal dialysis solution would diffuse through the encapsulation where it would be adsorbed by the strong acid or dual-property resin. The positive counter ions produced would be adsorbed by the weak base resin also present in the encapsulation or by the dual-property resin. Divalent positively charged calcium and magnesium ions in the peritoneal dialysis solution would be prevented from passing through the ion-rejecting encapsulation. The encapsulation could be comprised of the materials previously discussed that would reject calcium and magnesium ions by electrostatic repulsion (e.g., positively charged polymers), hydrophobicity (e.g., fatty acids) or size exclusion (e.g., cellulose acetate).

Urea can also be removed from the peritoneal dialysis solution using one or more enzymes that degrade urea. Thus, in another embodiment, the urea removal layer is comprised of an enzyme that degrades urea, an ion exchange sorbent that absorbs the urea degradation products and a composition that rejects divalent positive ions, specifically calcium and magnesium. The enzyme can be any known to one of skill in the art that can break down urea into its ionic components (e.g., ammonium and carbonate ions). Enzymes with the correct specificity and activity that can be employed are those naturally occurring (e.g., urease from jack beans), produced by recombinant technology (e.g., in bacterial, fungal, insect or mammalian cells that express and/or secrete urea-degrading enzymes) or produced synthetically (e.g., synthesized). In one embodiment, the enzyme is urease. In a particular embodiment, the enzyme (e.g., urease, urea amidolyase) is surrounded by an encapsulation, the encapsulation being any polymer appropriate for use in the device.

Figure 5:
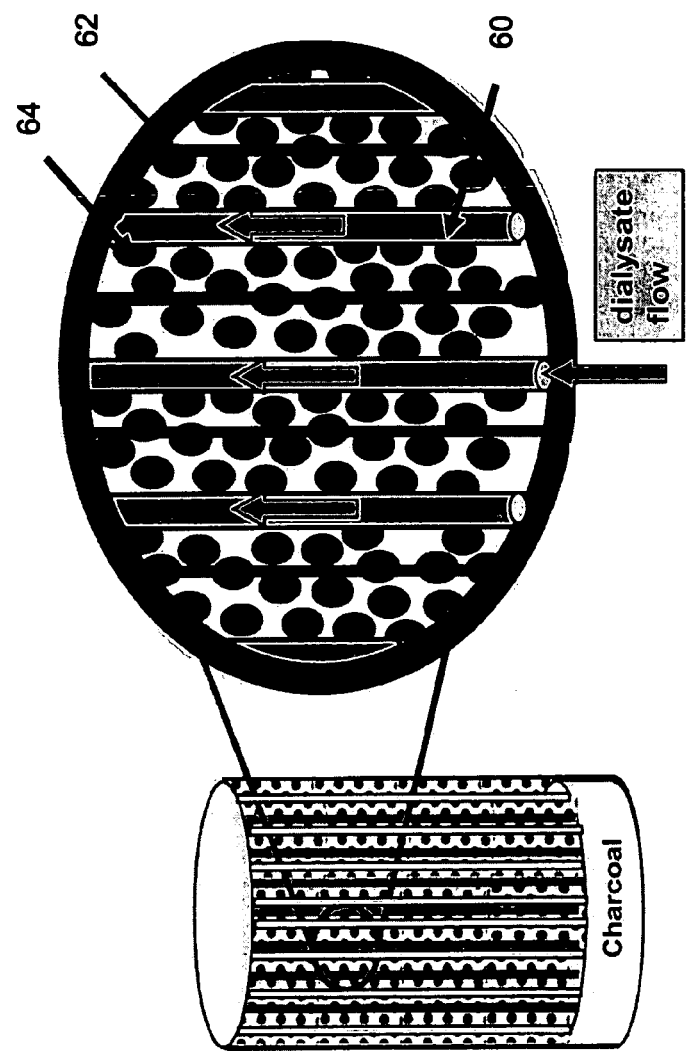
FIG. 5 is a drawing illustrating a hollow fiber device in a replaceable cartridge that contains urease to degrade urea and a sorbent to adsorb the ammonium produced by urea degradation.

In the embodiment involving the use of urea-degradation enzymes, the composition that rejects calcium and magnesium ions can similarly be hollow fibers coated with an ion-rejecting material or hollow fibers comprised of an ion-selective nanofiltration membrane as described above. Alternatively, the ions can be rejected by an encapsulation surrounding the urea degrading enzyme and the ion exchange sorbent. In the embodiment shown in FIG. 5, peritoneal dialysis solution containing urea flows through hollow fibers 60. Urea passes through hollow fibers 60, where encapsulated enzymes 62 break down the urea into ammonium and carbonate, the urea degradation byproducts absorbed by ion exchange sorbent 64. The sorbent (e.g., a cation exchange resin) absorbs the ammonium ions in exchange for sodium and hydrogen ions. In a preferred embodiment, the ion exchange sorbent is zirconium phosphate, but can be any ion exchange sorbent that can effectively absorb urea degradation products. As in the previous embodiment with the strong acid and weak base resins, hollow fibers 60 allow the urea in the peritoneal dialysis solution to diffuse through and reject positively charged ions in the solution. If the urea-degrading enzyme and ion exchange sorbent are surrounded by an ion-selective encapsulation (as opposed to the urea removal layer containing hollow fibers), the urea in the peritoneal dialysis solution diffuses through the encapsulation, where it is degraded by the enzyme and those degradation products are then bound by the ion-exchange sorbent. The ion-selective encapsulation rejects the calcium and magnesium ions in the peritoneal dialysis solution, so that they are retained in the solution. The ion-rejecting material coating the hollow fibers or comprising the encapsulation surrounding the enzyme and ion exchange resin would typically do so by electrostatic repulsion, hydrophobicity or size exclusion.

The replaceable cartridge is further comprised of an ion exchange layer 38 (see FIGS. 1 and 2), which is designed to remove phosphate and sulfate from the peritoneal dialysis fluid after urea removal. The ion exchange layer can be comprised of these ion exchange resins able to remove phosphate and/or sulfate, for example, a strong base anion exchange resin and other applicable forms of the resin such as carbonate, bicarbonate or chloride. These resins are known to the skilled artisan who can determine the most favorable resin for use in the invention based on a number of factors, including the patient's condition and the physiological advantages of using a particular resin and the potential toxicity of the resin. For instance, the ion exchange resin could be a polymeric/polyamine phosphate binder like sevelamer hydrochloride (i.e., Renagel®, Genzyme, Inc.) poly(allylamine) and/or poly (allylamine hydrochloride). Other commercially available ion exchange resins useful for binding phosphate include: DOWEX M-43 (anion exchange resin), DOWEX 21 K XLT, DOWEX Marathon MSA and DOWEX M4195 (in the copper form). Alternatively, the ion exchange layer can be comprised of an anion exchange resin that would bind phosphate and sulfate (e.g., Amberlite™ 96, Rohm and Haas) and, in a particular embodiment, is zirconium oxide or a useful form of zirconium oxide (e.g., hydrous zirconium oxide in the acetate counter ion form combined with zirconium carbonate).

Thus, after flowing through the replaceable cartridge of the invention, the peritoneal dialysis solution is essentially regenerated for reuse. The solution is largely free of urea, uric acid and creatinine, and has lower levels of phosphate, sulfate and potassium. Due to the design of the urea removal layer such that its components reject particular ions, the peritoneal dialysis solution retains the calcium and magnesium ions essential to the patient, eliminating the need for a mechanism to replace these ions in the patient.

The invention further relates to methods for the removal of uremic waste metabolites from a patient using a wearable peritoneal dialysis system. The method comprises providing a volume of peritoneal dialysis solution to the patient; pumping the peritoneal dialysis solution into the peritoneal cavity of the patient through an access port and allowing the patient's uremic waste metabolites to diffuse across the peritoneal membrane into the peritoneal dialysis solution; draining excess fluid into a replaceable drain container; filtering particulates and debris from the peritoneal dialysis solution containing uremic waste metabolites; regenerating the peritoneal dialysis solution containing uremic waste metabolites using a replaceable cartridge, the cartridge having an urea removal layer that rejects calcium and magnesium ions; and returning the regenerated peritoneal dialysis solution to the patient's peritoneal cavity.

The access ports through which the peritoneal dialysis solution is added and removed can be at a convenient and appropriate place in the patient's peritoneal cavity and can be connected to the wearable peritoneal dialysis system by any appropriate medical tubing, a double lumen catheter or a single lumen catheter. The volume of peritoneal dialysis solution initially provided in the wearable peritoneal dialysis system can be anywhere from 0.5 to 2 liters, or whatever volume deemed to be suitable to effectively clear uremic waste metabolites from the patient by one with skill in the art. The peritoneal dialysis solution can be pumped through the dialysis system at a rate of about 50 to 500 mL/min and the dialysis can occur continuously or semi-continuously. In a particular embodiment of the method, drainage of excess fluid from the patient occurs at a rate of about 0.5 to 2 liters per 24 hour period. If the wearable dialysis system operates continuously, as in one embodiment of the invention, the drainage of excess fluid could also be continuous, with excess fluid being periodically removed from the replaceable drain container by the patient. Alternatively, the dialysis system can operate semi-continuously for a specific period of time (e.g., 20 hours) and the removal of excess fluid take place during a period of time subsequent to the dialysis (e.g., 4 hours). Preferably, some fresh dialysis fluid is added to the wearable kidney system once a day at a convenient time.

The peritoneal dialysis solution provided is regenerated by a replaceable cartridge having a urea removal layer that rejects calcium and magnesium ions. As before, regeneration of the peritoneal dialysis solution allows the amount of solution necessary to perform the dialysis to be small and the wearable peritoneal dialysis system to weigh little enough to be easily wearable. The replaceable cartridge is as described previously and regenerates the peritoneal dialysis solution through the use of a series of layers in the device, the first removing heavy metals, oxidants and other uremic waste metabolites from the solution in a purification layer, the next eliminating urea from the solution without removing essential ions in a urea removal layer and the last removing phosphate and sulfate from the peritoneal dialysis solution in an ion exchange layer. The components of the replaceable cartridge that perform these functions are those described previously, that is, activated carbon (in the purification layer), a polymeric phosphate binder or an ion exchange resin (in the ion exchange layer) and urea removal components (e.g., strong acid and weak base resin(s) or urea-degrading enzymes and an ion exchange sorbent) together with a composition that rejects calcium and magnesium ions (e.g., hollow fibers coated with an ion-rejecting material, hollow fibers comprised of an ion-selective nanofiltration membrane or an encapsulation surrounding the urea removal components) (in the urea removal layer). In a preferred embodiment, the ion-rejecting material coating the hollow fibers or surrounding the resins and/or enzymes is positively charged and, in particular, can be cellulose triacetate, fatty acids or polymer chains.

In addition, the method can further comprise orally administering to a patient a source of one or more enzymes capable of degrading uremic waste metabolites, enzymes like uricase, urease or creatininase. In doing so, the load of uremic waste metabolites that need to be removed from the patient by the wearable peritoneal dialysis system can be significantly reduced in amount or altered for ease of removal and/or intestinal elimination. The source of the orally administered enzymes can be the one or more enzymes themselves in an acceptable pharmaceutical carrier and/or in a suitable encapsulation, or naturally occurring or genetically engineered cells that can degrade uremic waste metabolites as described previously. Preferably, the enzymes together with the sorbent are administered in an encapsulated form and in some cases, this encapsulation can also reject calcium and magnesium ions. The amount and/or dosage of the source of uremic toxin-degrading enzymes administered to the patient can be appropriately determined by one with skill in the art, and is dependent on the formulation chosen, the assessed necessity to clear a particular amount of uremic waste metabolites from the patient and the patient's specifications (e.g., age, body weight and overall well-being).

The source of one or more enzymes, together with the wearable peritoneal dialysis system preferably results in urea being cleared from the patient at a rate of about 10 to 15 mL/min and phosphate being cleared from the patient at a rate of about 8 to 12 mL/min. Sulfate is preferably cleared from the patient at a rate of about 50 mEq per 24 hours and hydrogen ions are preferably cleared from the patient at a rate of about 60 to 70 mEq in a 24 hour period.

In yet another embodiment of the method, glucose is added to the regenerated peritoneal dialysis solution in a mix container to ensure proper osmotic flow in the patient's peritoneal cavity. Accordingly, the method further comprises infusing a glucose solution into the mix container via a flow pump between the on-off switch and the mix container, the pump regulating the flow of the regenerated peritoneal dialysis solution into the mix container; mixing the regenerated peritoneal dialysis solution with the glucose solution in the mix container; and pumping the re-mixed and regenerated peritoneal dialysis solution back into the dialysis system.

In a further embodiment of the method, the re-mixed and regenerated peritoneal dialysis solution is filtered to remove bacterial contamination from the solution. In yet another embodiment, the re-mixed and regenerated peritoneal dialysis solution flows through a three-way valve into an initial priming point of the dialysis system before the peritoneal dialysis solution is returned to the patient's peritoneal cavity.

To consistently and efficiently remove uremic waste metabolites from a patient, control of the wearable peritoneal dialysis system and, in particular, the pump flow rates and the timing and sequencing of the components of the dialysis system are electrically controlled. In a preferred embodiment, the control mechanism is a microprocessor which is part of a unit containing the dialysis system that is under its own control; however, the microprocessor can also be controlled wirelessly, typically by another microprocessor.

While this invention has been particularly shown and described with references to preferred embodiments thereof, it will be understood by those skilled in the art that various changes in form and details may be made therein without departing from the scope of the invention encompassed by the appended claims.

What is claimed is:

1. A wearable peritoneal dialysis system for a patient comprising:
    a volume of peritoneal dialysis solution that is infused into and moved out of the patient's peritoneal cavity, thereby removing from the patient uremic waste metabolites that have diffused into the peritoneal dialysis solution;

a closed fluid system loop for circulating the peritoneal dialysis solution from the patient, throughout the system and back into the patient;

at least one pump for infusing the peritoneal dialysis solution into the patient's peritoneal cavity and moving the peritoneal dialysis solution containing uremic waste metabolites out of the patient's peritoneal cavity and into the fluid system loop; and a replaceable cartridge in the fluid system loop for receiving the peritoneal dialysis solution containing uremic waste metabolites from the patient's peritoneal cavity and for regenerating the peritoneal dialysis solution, said replaceable cartridge having an urea removal layer that includes an ion-selective element comprised of hollow fibers coated with an ion-selective material that prevents calcium from being removed from the peritoneal dialysis solution, the peritoneal dialysis solution flowing through the hollow fibers in the closed fluid system loop.

2. The wearable peritoneal dialysis system of claim 1, wherein the ion-selective element prevents calcium and magnesium from being removed from the peritoneal dialysis solution.

3. The wearable peritoneal dialysis system of claim 2, wherein the ion-selective element comprises:
a cation exchange sorbent to adsorb the urea; and
an anion exchange sorbent to adsorb the counter ions released by the adsorption of urea by said cation exchange sorbent.

4. The wearable peritoneal dialysis system of claim 3, wherein the cation exchange sorbent includes a strong acid cation exchange resin, and the anion exchange sorbent includes a weak base anion exchange resin.

5. The wearable peritoneal dialysis system of claim 3, wherein a dual-property sorbent is both the cation exchange sorbent and the anion exchange sorbent.

6. The wearable peritoneal dialysis system of claim 1, wherein the ion-selective material is cellulose acetate.

7. The wearable peritoneal dialysis system of claim 2, wherein the ion-selective element is an ion-selective nanofiltration material.

8. The wearable peritoneal dialysis system of claim 7, wherein the ion-selective nanofiltration material rejects calcium and magnesium ions.

9. The wearable peritoneal dialysis system of claim 2, wherein the ion-selective element is an ion-selective nanofiltration membrane.

10. The wearable peritoneal dialysis system of claim 9, wherein the ion-selective nanofiltration membrane rejects calcium and magnesium ions.

11. The wearable peritoneal dialysis system of claim 2, further including a replaceable drain container attached to the fluid system loop for draining excess fluid.

12. The wearable peritoneal dialysis system of claim 11, further including a filter attached to the fluid system loop for removing particulates and debris from the peritoneal dialysis solution containing uremic waste metabolites.

13. The wearable peritoneal dialysis system of claim 2, wherein the system is used in conjunction with a source of one or more enzymes that degrade uremic waste metabolites, the source of one or more enzymes orally administered to the patient, thereby reducing the load of uremic waste metabolites to be removed from the patient by the system.

14. The wearable peritoneal dialysis system of claim 13, wherein the source of the one or more enzymes is a cell selected from the group consisting of a microbial cell, a yeast cell and a mammalian cell.

15. The wearable peritoneal dialysis system of claim 13, wherein the one or more enzymes are selected from the group consisting of urease, creatininase and uricase.

16. The wearable peritoneal dialysis system of claim 2, wherein the replaceable cartridge further includes:
a purification layer for removing heavy metals, oxidants and other uremic waste metabolites from said peritoneal dialysis solution; and
an ion-exchange layer for removing phosphate and sulfate from said peritoneal dialysis solution.

17. The wearable peritoneal dialysis system of claim 2, wherein the urea removal layer comprises urea removal components selected from the group consisting of: a cation exchange sorbent together with an anion exchange sorbent, a dual-property sorbent and a urea-degradation enzyme together with an ion exchange sorbent.

18. The wearable peritoneal dialysis system of claim 17, wherein the ion exchange sorbent is zirconium phosphate.

19. The wearable peritoneal dialysis system of claim 17, wherein the cation exchange sorbent includes a strong acid cation exchange resin, and the anion exchange sorbent includes a weak base anion exchange resin.

20. The wearable peritoneal dialysis system of claim 17, wherein the dual-property sorbent is both the cation exchange sorbent and the anion exchange sorbent.

21. The wearable peritoneal dialysis system of claim 17, wherein the urea removal layer further comprises a composition that rejects calcium and magnesium ions selected from the group consisting of: hollow fibers comprised of an ion-selective nanofiltration membrane, hollow fibers coated with a material that rejects calcium and magnesium ions and an encapsulation surrounding the urea removal components, the encapsulation comprised of a material that rejects calcium and magnesium ions.

22. The wearable peritoneal dialysis system of claim 21, wherein the hollow fibers are coated with cellulose acetate.

23. The wearable peritoneal dialysis system of claim 21, wherein each layer of the cartridge is removable and replaceable.

24. The wearable peritoneal dialysis system of claim 23, further comprising a mix container attached to the fluid system loop to re-mix the regenerated peritoneal dialysis solution with glucose.

25. The wearable peritoneal dialysis system of claim 24, further comprising a three-way valve to connect the flow of the re-mixed and regenerated peritoneal dialysis solution to an initial priming point of the fluid system loop.

26. The wearable peritoneal dialysis system of claim 25, further comprising a filter attached to the fluid system loop to remove bacterial contamination from the regenerated peritoneal dialysis solution.

27. The wearable peritoneal dialysis system of claim 26, further comprising a microprocessor in communication with the components of the fluid system loop, said microprocessor controlling the pump flow rates and the timing and sequencing of the components of the dialysis system.

28. In a wearable peritoneal dialysis system for a patient having
a volume of peritoneal dialysis solution that is infused into and moved out of the patient's peritoneal cavity, thereby removing from the patient uremic waste metabolites that have diffused into the peritoneal dialysis solution,
a closed fluid system loop for circulating the peritoneal dialysis solution from the patient, throughout the system and back into the patient, and
at least one pump for infusing the peritoneal dialysis solution into the patient's peritoneal cavity and moving the peritoneal dialysis solution containing uremic waste metabolites out of the patient's peritoneal cavity and into the fluid system loop, the improvement comprising a replaceable cartridge in the fluid system loop for receiving the peritoneal dialysis solution containing uremic waste metabolites from the patient's peritoneal cavity and for regenerating the peritoneal dialysis solution, said replaceable cartridge having an urea removal layer that includes an ion-selective element comprised of hollow fibers coated with an ion-selective material that prevents calcium from being removed from the peritoneal dialysis solution, the peritoneal dialysis solution flowing through the hollow fibers in the closed fluid system loop.

29. The improvement of claim 28, wherein the ion-selective element prevents calcium and magnesium from being removed from the peritoneal dialysis solution.

30. The improvement of claim 29, wherein the ion-selective element is an ion-selective nanofiltration material.

31. The improvement of claim 30, wherein the ion-selective nanofiltration material rejects calcium and magnesium ions.

32. The improvement of claim 29, wherein the ion-selective element is an ion-selective nanofiltration membrane.

33. The improvement of claim 32, wherein the ion-selective nanofiltration membrane rejects calcium and magnesium ions.

34. A replaceable cartridge for regenerating peritoneal dialysis solution comprising:
    a purification layer for removing heavy metals, oxidants and other uremic waste metabolites from said peritoneal dialysis solution;
    a urea removal layer that includes an ion-selective element comprised of hollow fibers coated with an ion-selective material that prevents calcium from being removed from the peritoneal dialysis solution, the peritoneal dialysis solution flowing through the hollow fibers; and
    an ion-exchange layer for removing phosphate and sulfate from said peritoneal dialysis solution.

35. The replaceable cartridge of claim 34, wherein the ion-selective element prevents calcium and magnesium from being removed from the peritoneal dialysis solution.

36. A method for the removal of uremic waste metabolites from a patient using a wearable peritoneal dialysis system comprising:
    providing a volume of peritoneal dialysis solution;
    pumping the peritoneal dialysis solution into the peritoneal cavity of the patient through an access port, allowing the patient's uremic waste metabolites to diffuse across the peritoneal membrane into the peritoneal dialysis solution;
    pumping the peritoneal dialysis solution containing uremic waste metabolites out of the patient and into the system;
    regenerating the peritoneal dialysis solution containing uremic waste metabolites using a replaceable cartridge having an urea removal layer that includes an ion-selective element comprised of hollow fibers coated with an ion-selective material that prevents calcium from being removed from the peritoneal dialysis solution the peritoneal dialysis solution flowing through the hollow fibers; and
    returning the regenerated peritoneal dialysis solution to the patient's peritoneal cavity.

37. The method of claim 36, wherein the ion-selective element prevents calcium and magnesium from being removed from the peritoneal dialysis solution.

38. A wearable peritoneal dialysis system for a dialysis patient comprising:
    a dialysis solution loop for circulating a peritoneal dialysis solution into the peritoneal cavity of the patient and from the patient's peritoneal cavity through the system and back into the patient;
    a replaceable cartridge in the dialysis solution loop for receiving the peritoneal dialysis solution containing uremic waste metabolites from the patient's peritoneal cavity and for regenerating the peritoneal dialysis solution, said replaceable cartridge having an urea removal layer that includes an ion-selective element comprised of hollow fibers coated with an ion-selective material that reduces calcium removal from the peritoneal dialysis solution in the replaceable cartridge, the peritoneal dialysis solution flowing through the hollow fibers in the dialysis solution loop; and
    at least one pump for infusing regenerated peritoneal dialysis solution into the patient's peritoneal cavity and removing the peritoneal dialysis solution containing uremic waste metabolites from the patient's peritoneal cavity and circulating it through the replaceable cartridge and back to the patient's peritoneal cavity.

* * * * *